United States Patent
Johnson

(10) Patent No.: US 12,329,624 B2
(45) Date of Patent: Jun. 17, 2025

(54) INFLATABLE MEDICAL IMPLANT HAVING A PRESSURE MONITOR

(71) Applicant: Boston Scientific Scimed, Inc., Maple Grove, MN (US)

(72) Inventor: Richard E. Johnson, New Prague, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 903 days.

(21) Appl. No.: 17/449,851

(22) Filed: Oct. 4, 2021

(65) Prior Publication Data

US 2022/0110734 A1    Apr. 14, 2022

Related U.S. Application Data

(60) Provisional application No. 63/198,283, filed on Oct. 8, 2020.

(51) Int. Cl.
*A61F 2/00* (2006.01)

(52) U.S. Cl.
CPC ...... *A61F 2/004* (2013.01); *A61F 2250/0002* (2013.01); *A61F 2250/0003* (2013.01); *A61F 2250/0013* (2013.01)

(58) Field of Classification Search
CPC ...... A61F 2250/0002; A61F 2250/0003; A61F 2/0013; A61F 2/0004; A61F 2/0031; A61F 2/004; A61F 2/0045
See application file for complete search history.

(56) References Cited

U.S. PATENT DOCUMENTS

| | | | |
|---|---|---|---|
| 2003/0100929 A1* | 5/2003 | Forsell | A61F 2/26 607/39 |
| 2011/0015738 A1* | 1/2011 | Vaingast | A61F 2/004 623/14.13 |
| 2017/0079760 A1* | 3/2017 | Newman | A61F 2/26 |
| 2019/0374344 A1 | 12/2019 | Forsell | |

FOREIGN PATENT DOCUMENTS

WO    2020150097 A1    7/2020

OTHER PUBLICATIONS

Fonseca, et al., "Flexible Wireless Passive Pressure Sensors for Biomedical Applicatons", Solid-State Sensors, Actuators, and Microsystems Workshop, Hilton Head Island, South Carolina, Jun. 4-8, 2006, pp. 37-42.

Fonseca, et al., "Wireless Micromachined Ceramic Pressure Sensor for High-Temperature Applications", Journal of Microelectromechanical Systems, vol. 11, No. 4, Aug. 2002, pp. 337-343.

International Search Report and Written Opinion for PCT Application No. PCT/US2021/071746, mailed on Jan. 20, 2022, 13 pages.

* cited by examiner

*Primary Examiner* — Samuel G Gilbert
(74) *Attorney, Agent, or Firm* — Brake Hughes Bellermann LLP

(57) ABSTRACT

According to an aspect, an apparatus includes a bodily implant configured to be implanted into a body of a patient, the implant including an inflatable member and a sending unit, the sending unit having a sensor configured to sense the pressure of the inflation member; and a reading unit, the reading unit configured to be disposed outside of the body of the patient and configured to operatively communicate with the sending unit.

17 Claims, 9 Drawing Sheets

```
                    600

┌─────────────────────────────────────┐
        │   Connect reading unit to display device │
        │                 610                  │
        └─────────────────────────────────────┘
                          │
        ┌─────────────────────────────────────┐
        │  Place reading unit in proximity to the sending unit │
        │                 620                  │
        └─────────────────────────────────────┘
                          │
        ┌─────────────────────────────────────┐
        │ Inflate or deflate the inflation member of the body implant │
        │                 630                  │
        └─────────────────────────────────────┘
```

FIG. 9

INFLATABLE MEDICAL IMPLANT HAVING A PRESSURE MONITOR

CROSS-REFERENCE TO RELATED APPLICATION

This application claims priority to U.S. Provisional Patent Application No. 63/198,283, filed on Oct. 8, 2020, entitled "INFLATABLE MEDICAL IMPLANT HAVING A PRESSURE MONITOR", the disclosure of which is incorporated by reference herein in its entirety.

TECHNICAL FIELD

This disclosure relates generally to a medical device having an inflatable member and a pressure sensor.

BACKGROUND

In some medical devices, an inflatable member or portion is used to apply pressure to a portion of the body. For example, in some medical devices, an inflatable member or portion is used to apply pressure to a urethra of a patient. In some cases, the medical device may not function properly or may cease working while the device is within the body of the patient.

Accordingly, there is a need for a medical device that may be inflated within the body of the patient and includes a device or a sensor to provide to the physician, the health care provider, the user, or a patient the amount of pressure that is being applied by the medical device or a portion of the medical device (such as an inflatable portion of the medical device).

SUMMARY

According to an aspect, an apparatus includes a bodily implant configured to be implanted into a body of a patient, the implant including an inflatable member and a sending unit, the sending unit having a sensor configured to sense the pressure of the inflation member; and a reading unit, the reading unit configured to be disposed outside of the body of the patient and configured to operatively communicate with the sending unit.

In some embodiments, the bodily implant includes a pump and a reservoir. In one embodiment, the bodily implant includes a pump and a reservoir, the pump being configured to pump fluid from the reservoir to the inflatable member. In another embodiment, the bodily implant includes a pump, a reservoir, a first tubular member extending between the pump and the inflatable member, and a second tubular member extending between the pump and the reservoir. In another embodiment, the bodily implant includes a pump, a reservoir, a first tubular member and a second tubular member, the first tubular member having a first portion and a second portion, the first portion of the first tubular member extending between the pump and the inflatable member, the second portion of the first tubular member being operatively coupled to the sending unit, the second tubular member extending between the pump and the reservoir.

In some embodiments, the bodily implant includes a pump and a reservoir, a first tubular member is coupled to and extends between the pump and the reservoir, a second tubular member is coupled to and extends between the inflatable member and a Y connector, a third tubular member is coupled to and extends between the sending unit and the Y connector, and a fourth tubular member is coupled to and extends between the pump and the Y connector.

In some embodiments, the sending unit includes a pressure sensor, a sending coil, the reading unit includes a receiving coil and a power source. In some embodiments, the reading unit is configured to communicate with a display device. In some embodiments, the reading unit is configured to communicate wirelessly with a display device.

In some embodiments, the inflatable member is configured to form a ring. In some embodiments, the inflatable member is a cuff. In some embodiments, the bodily implant is configured to be disposed within a pelvic region of the patient and inflatable member is configured to be disposed adjacent a urethra of the patient.

In some embodiments, the bodily implant is devoid of an electrical power source.

In some embodiments, the bodily implant includes a pump, the sending unit being operatively coupled between the pump and the inflatable member. In some embodiments, the bodily implant includes a pump, the sending unit being operatively coupled between and spaced from the pump and the inflatable member.

According to another aspect a kit includes a bodily implant configured to be implanted into a body of a patient, the implant including an inflatable member, a pump, and a sending unit, the sending unit having a sensor configured to sense the pressure of the inflation member, the sending unit being devoid of an electrical power source; and a reading unit, the reading unit configured to be disposed outside of the body of the patient and configured to operatively communicate with the sending unit, the reading unit including a power source.

In some embodiments, the pump is fluidically coupled to the inflatable member and the sending unit.

In some embodiments, the bodily implant includes a tubular member that includes a first portion and a second portion, the first portion of the tubular member is coupled to and extends between the pump and the inflatable member, the second portion is coupled to the sending unit.

In some embodiments, the reading unit is configured to communicate with a display device.

According to another aspect a kit includes, a bodily implant configured to be implanted into a body of a patient, the implant including an inflatable member, a pump, and a sending unit, the sending unit having a sensor configured to sense the pressure of the inflation member, the sending unit being devoid of an electrical power source; and a reading unit, the reading unit configured to be disposed outside of the body of the patient and configured to operatively communicate with the sending unit, the reading unit including a power source, the reading unit being configured to wirelessly communicate with a display device.

BRIEF DESCRIPTION OF THE DRAWINGS

FIG. 9 is a flow chart of a method according to an embodiment of the invention.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The bodily implant disclosed herein are configured to be disposed within a body of a patient. In some embodiments, the bodily implant includes an inflatable member or inflation member. In some embodiments, the inflatable member is configured to be inflated to place pressure on a portion of the body of the patient. In some embodiments, the bodily implant may be placed within a pelvic region of a patient. In some embodiments, the bodily implant is an artificial urinary sphincter and the inflatable member is configured to place pressure on a urethra of a patient. In other embodiments, the implant may be another type of implant. For example, the bodily implant may be a penile implant and the inflatable member may be configured to be disposed within a penis of a patient. In other embodiments, the bodily implant is configured to be placed in a different region of the body of the patient and is configured to place pressure on a different portion of the body of the patient.

Figure 1:
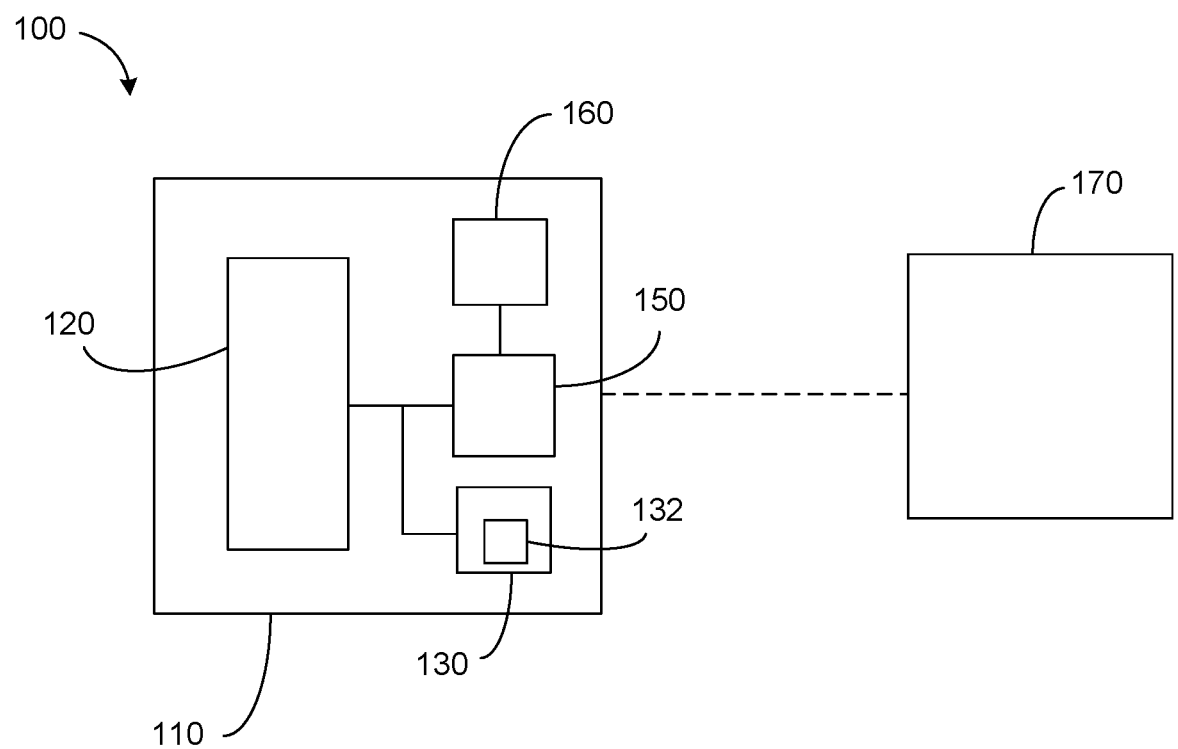
FIG. 1 schematically illustrates an apparatus according to an embodiment of the invention.

FIG. 1 illustrates an apparatus 100 according to an embodiment of the invention. In the illustrated embodiment, the apparatus 100 includes a bodily implant 110 and a reading unit 170. The bodily implant 110 is configured to be disposed or otherwise placed within a body of a patient. In some embodiments, the bodily implant is configured to be placed within a pelvic region of a patient. For example, in some embodiments, the bodily implant is a configured to be placed within a pelvic region of a patient and is configured to address or help treat continence issues of the patient, such as urinary incontinence or fecal incontinence. The reading unit 170 is configured to be disposed outside of the body of the patient. The reading unit 170 is configured to communicate with the bodily implant.

In the illustrated embodiment, the bodily implant 110 includes an inflatable or inflation member 120 and a sending unit 130. The inflatable member 120 is configured to be placed in an inflated configuration and a deflated configuration. In some embodiments, the inflatable member 120 is configured to place pressure on a portion of the body of the patient when the inflatable member 120 is in its inflated configuration. For example, in some embodiments, the inflatable member 120 is configured to be disposed proximate a urethra of a patient and is configured to serve as an artificial sphincter. In such an embodiment, the inflatable member 120 applies a pressure to the urethra when the inflatable member 120 is in its inflated configuration and does not apply a pressure (or less of a pressure) when the inflatable member 120 is in is deflated configuration.

In some embodiments, the inflatable member 120 is formed of a material that is configured to expand. In some embodiments, the inflatable member 120 is a balloon or other inflatable type device. In some embodiments, the inflatable member 120 is or forms a loop or circle and is configured to surround a portion of the body of the patient, such as a urethra of a patient.

The sending unit 130 is operatively coupled to the inflatable member 120 and is configured to sense or detect the pressure within the inflatable member 120. In the illustrated embodiment, the sending unit 130 includes a pressure sensor 132 that is configured to detect or sense the pressure within the inflatable member 120. For example, in some embodiments, the pressure sensor 132 is configured to sense or detect a fluidic pressure within the inflatable member 120.

The reading unit 170 is configured to communicate with the sending unit 130. In some embodiments, the reading unit 170 is configured to receive the pressure that is detected or sensed by the pressure sensor 132. In some embodiments, the reading unit 170 includes a power source, such as an electrical power source. For example, in some embodiments, the reading unit 170 includes a battery.

In some embodiments, the bodily implant 110 does not include a chemical power source, such as a battery. In other words, the bodily implant 110 is devoid of a battery. Specifically, in some embodiments, the sending unit 130 does not include an electrical power source, such as a battery. Accordingly, in such embodiments, the bodily implant may be placed or disposed within the body of the patient without the need to monitor or change a battery that is disposed within a body of the patient.

In the illustrated embodiment, the bodily implant 110 includes a pump 150 and a reservoir 160. The reservoir 160 is configured to house fluid in the system of the bodily implant 110. The pump 150 is operatively coupled to the inflatable member 120 and to the reservoir 160. The pump 150 is configured to pump or move fluid to the inflatable member 120 from the reservoir 160 to place the inflatable member 120 in its inflated configuration and to move fluid from the inflatable member 120 to the reservoir to place the inflatable member 120 in its deflated configuration. In the illustrated embodiment, the sending unit 130 is fluidically disposed between the pump 150 and the inflatable member 120.

In some embodiments, the reading unit 170 is configured to communicate with a display unit. The display unit may be a cell phone, table, smart watch, or other device with a display. In some embodiments, the reading unit 170 is configured to wirelessly communicate with the display unit. For example, in some embodiments, the reading unit 170 is configured to communicate with the display unit via Bluetooth.

Figure 2:
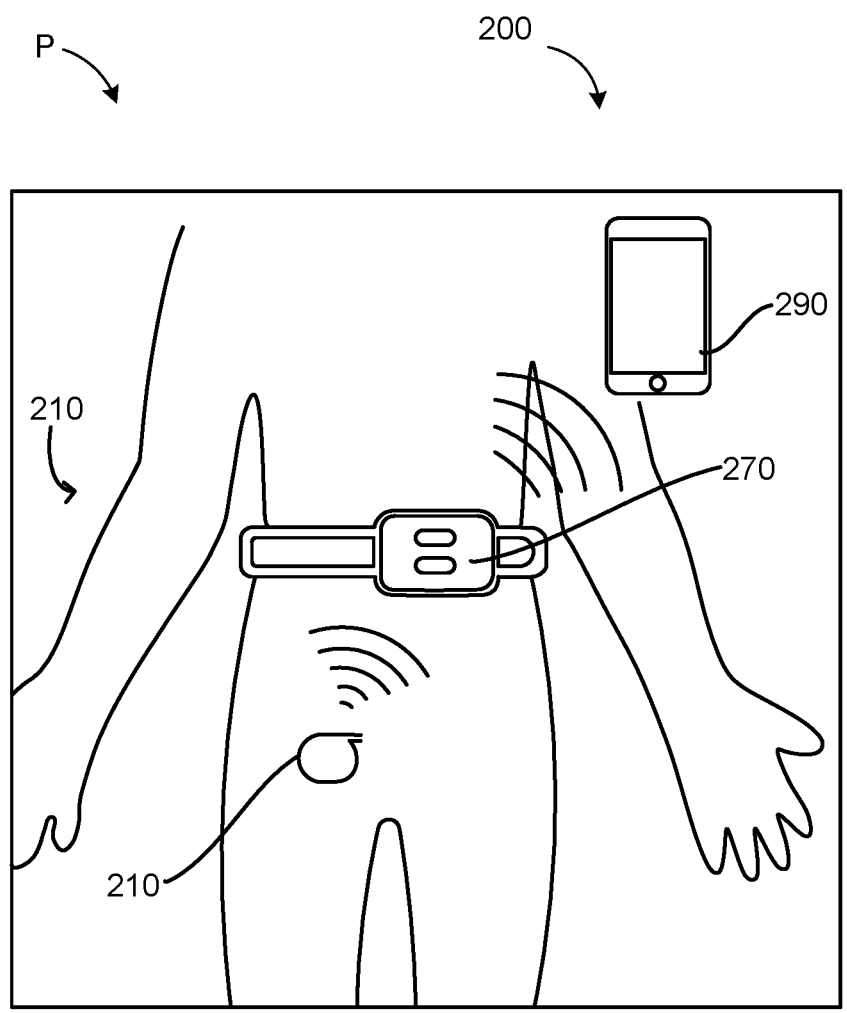
FIG. 2 is a schematically illustrates an apparatus in use within a patient according to an embodiment.

FIG. 2 illustrates an apparatus 200 in use according to an embodiment of the invention. The bodily implant 210 may be placed or disposed within the body of the patient. In the illustrated embodiment, the bodily implant 210 is disposed or placed within the body of the patient P. In some embodiments, the bodily implant 210 is disposed or placed within a pelvic region of a patient. In other embodiments, the bodily implant 210 is disposed or placed in a different location within the body of the patient P.

The reading unit 270 is disposed outside of the body of the patient P. The reading unit 270 is configured to communicate with the bodily implant 210 while the bodily unit 210 is disposed within the body of the patient. In some embodiments, the reading unit 270 includes an electrical power source, such as a battery, and is configured to energize or otherwise activate a sending unit of the bodily implant 210. Accordingly, the sending unit may then communicate or send information to the reading unit 270. In some embodiments, the reading unit 270 is configured to activate the sending unit when the reading unit 270 is placed or disposed within a distance from the sending unit.

In some embodiments, the reading unit 270 is configured to be worn or otherwise attached to the patient P or to an article or clothing of the patient P. For example, the reading unit 270 may be attached to a belt worn by the patient P, may be coupled to other clothing worn by the patient P, or may include a strap or other portion configured to be wrapped around a portion of the patient (such as around a wrist, a waist, or an ankle of the patient P).

In some embodiments, the reading unit 270 is configured to receive data regarding the bodily implant 210 from the sending unit. For example, in some embodiments, the reading unit 270 is configured to receive pressure data, such as fluidic pressure of the bodily implant 210 or a portion of the bodily implant 210.

The reading unit 270 is configured to communicate with a display device 290. In some embodiments, the display device 290 is configured to display to the patient or the physician the data of the bodily implant 210 that is received by the reading unit 270. For example, in some embodiment, the display device is configured to display the pressure data of the bodily implant. In some embodiments, the reading unit 270 is configured to wirelessly communicate with the display device 290. For example, in some embodiments, the reading unit 270 communicates with the display device 290 via Bluetooth, RF, or via another wireless system.

In some embodiment, the reading unit and the display device are housed in a single unit. In other words, the reading unit and the display device may be coupled together and/or housed by a single housing or component.

Figure 3:
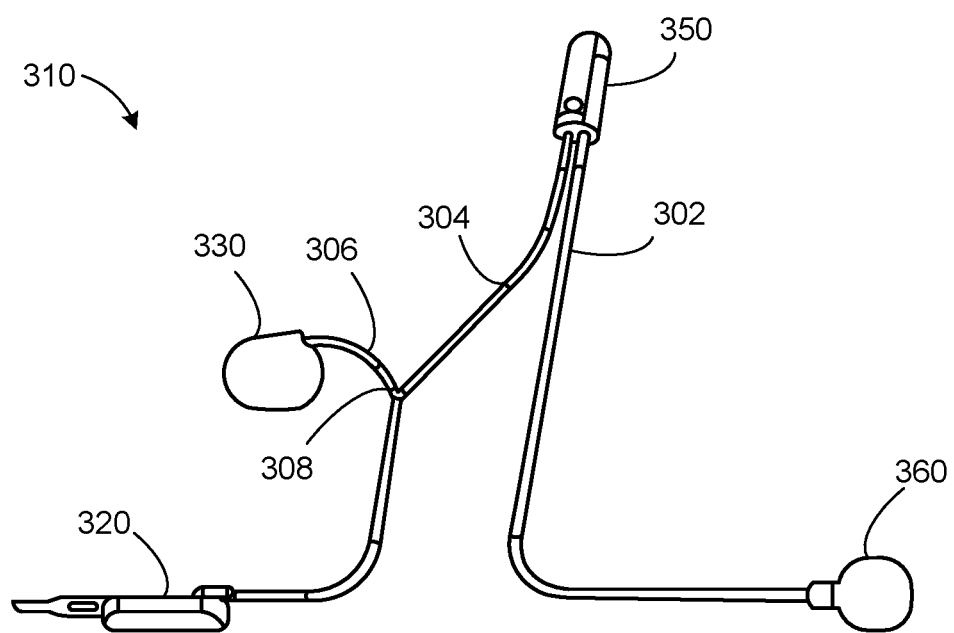
FIG. 3 illustrates a bodily implant according to an embodiment.
Figure 4:
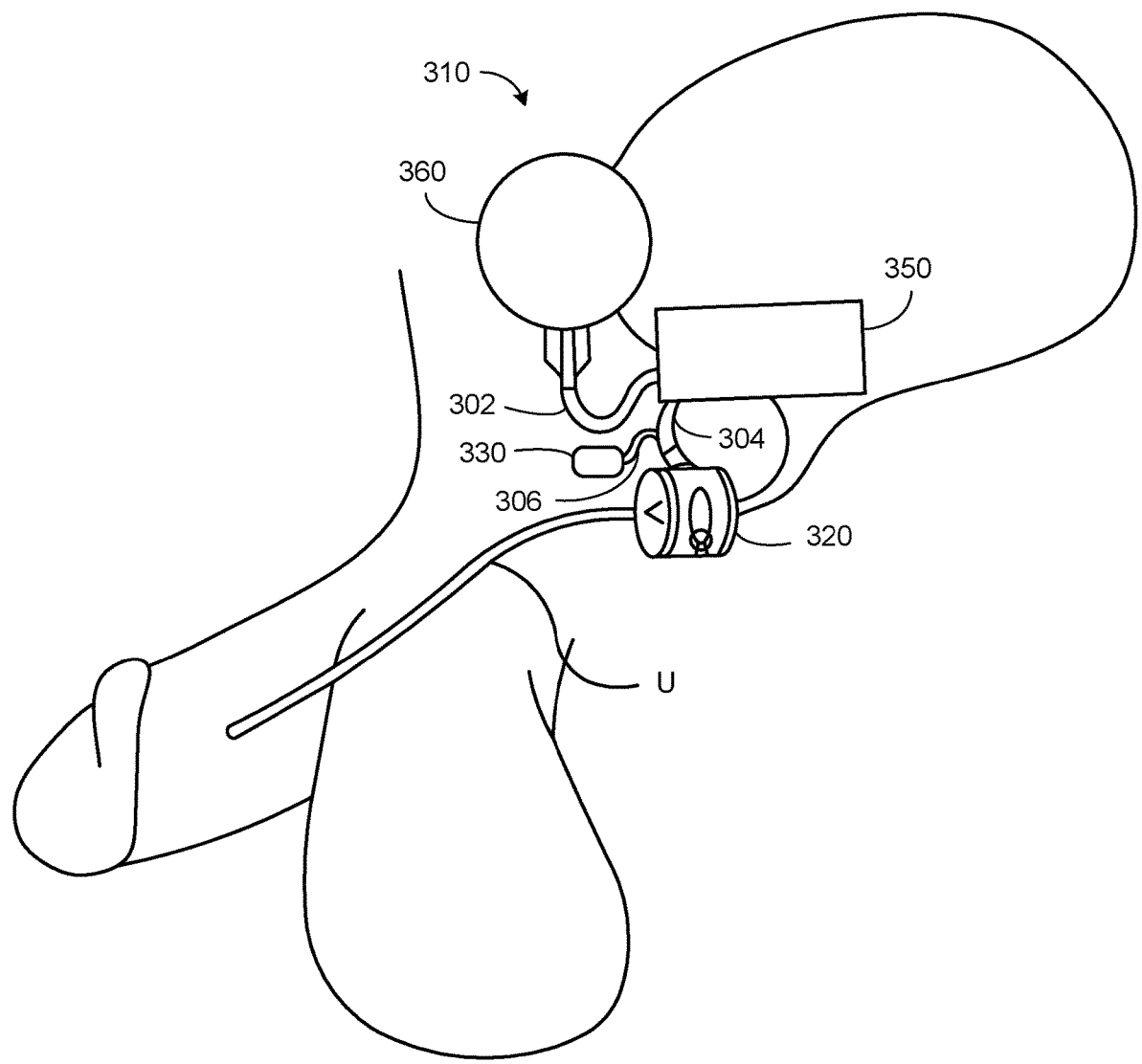
FIG. 4 illustrates the bodily implant of FIG. 3 disposed within a body of a patient.

FIG. 3 illustrates a bodily implant 310 according to an embodiment of the invention. In some embodiments, a bodily implant 310 may be used in the system or apparatus 200. The bodily implant 310 is configured to be disposed or otherwise placed within a body of a patient. In the illustrated embodiment, the bodily implant 310 is an artificial urinary sphincter and is configured to address or help treat urinary continence issues of the patient. FIG. 4 illustrates the bodily implant 310 disposed within a body of a patient. Specifically, the bodily implant 310 is disposed within the body of the patient such that an inflation member 320 is disposed proximate the urethra of the patient. Specifically, in the illustrated embodiment, the inflation member 320 is configured to surround or encircle the urethra U of the patient. Although FIG. 4 illustrates the bodily implant within a male patient, in other embodiments, the implant may be placed within a female patient.

In the illustrated embodiment, the bodily implant 310 includes the inflatable or inflation member 320 and a sending unit 330. The inflatable member 320 is configured to be placed in an inflated configuration and a deflated configuration. In the illustrated embodiment, the inflatable member 320 is configured to place pressure on the urethra of a patient and is configured to serve as an artificial sphincter. Specifically, the inflatable member 320 applies a pressure to the urethra when the inflatable member 320 is in its inflated configuration and does not apply a pressure (or applies less of a pressure) when the inflatable member 320 is in its deflated configuration.

In some embodiments, the inflatable member 320 is formed of a material that is configured to expand. In some embodiments, the inflatable member 320 is a balloon or other inflatable type device. As best illustrated in FIG. 4, in the illustrated embodiment, the inflatable member 320 is a cuff and is configured to form a loop or a circle. The inflatable member 320 is configured to surround a portion of the urethra of a patient.

In the illustrated embodiment, the bodily implant 310 also includes a pump 350 and a reservoir 360. The reservoir 360 is configured to house fluid in the system of the bodily implant 310. The pump 350 is operatively coupled to the inflatable member 320 and to the reservoir 360. The pump 350 is configured to pump or move fluid to the inflatable member 320 from the reservoir 360 to place the inflatable member 320 in its inflated configuration and to move fluid from the inflatable member 320 to the reservoir to place the inflatable member 320 in its deflated configuration. In some embodiments, the pump 350 includes a mode switch that may be used to switch from an inflate mode to a deflate mode. In the illustrated embodiment, the sending unit 330 is fluidically disposed between the pump 350 and the inflatable member 320.

In some embodiments, the pump 350 includes a bulb, a bulbous portion or other type of portion that is configured to be squeezed or depressed by the user in order to facilitate the transfer of fluid from the reservoir 360 to the inflatable member 320. For example, in the inflation mode, while the user is operating the pump bulb, the pump bulb may receive the fluid from the fluid reservoir, and then output the fluid to the inflatable member. When the user switches to the deflation mode, the user may squeeze the pump bulb to transfer of fluid back to the reservoir.

The reservoir 360 may be a pressure-regulating inflation balloon or element. The reservoir 360 may be constructed of polymer material that is capable of elastic deformation to reduce fluid volume within the fluid reservoir 360 and push fluid out of the fluid reservoir 360. In some embodiments, the reservoir 360 is made from an elastic material and is configured to expand when fluid is disposed in the reservoir 360. In some examples, the fluid reservoir 360 is implanted into the abdominal space.

The pump 350 is fluidically coupled between the reservoir 360 and the inflatable member 320. A first tubular member 302 is coupled to and extends between the pump 350 and the reservoir 360. The first tubular member 302 is configured to allow fluid to pass between the pump 350 and the reservoir 360. In some embodiments, the first tubular member 302 is a kink-resistant tube.

A second tubular member 304 is coupled to and extends between the pump 350 and the inflatable member 310. The second tubular member 304 is configured to allow fluid to pass between the pump 350 and the inflatable member 310. In some embodiments, the second tubular member 304 is a kink-resistant tube.

In the illustrated embodiment, the sending unit 330 is fluidically coupled between the pump 350 and the inflatable member 320. A third tubular member 306 is coupled to and extends between the second tubular member 304 and the sending unit 330. In some embodiments, the third tubular member 306 is a kink-resistant tube. In the illustrated embodiment, a Y connector 308 is coupled between the second tubular member 304 and the third tubular member 306.

The sending unit 330 is configured to sense or detect the pressure within the inflatable member 320. Specifically, in the illustrated embodiment, the sending unit 330 is configured to sense or detect the pressure within the tubular member 304 that extends between the pump 350 and the inflatable member 320. In the illustrated embodiment, the pressure within the tubular member 304 that extends between the pump 350 and the inflatable member 320 is the same as or substantially the same as the pressure within the inflatable member 320.

Figure 5:
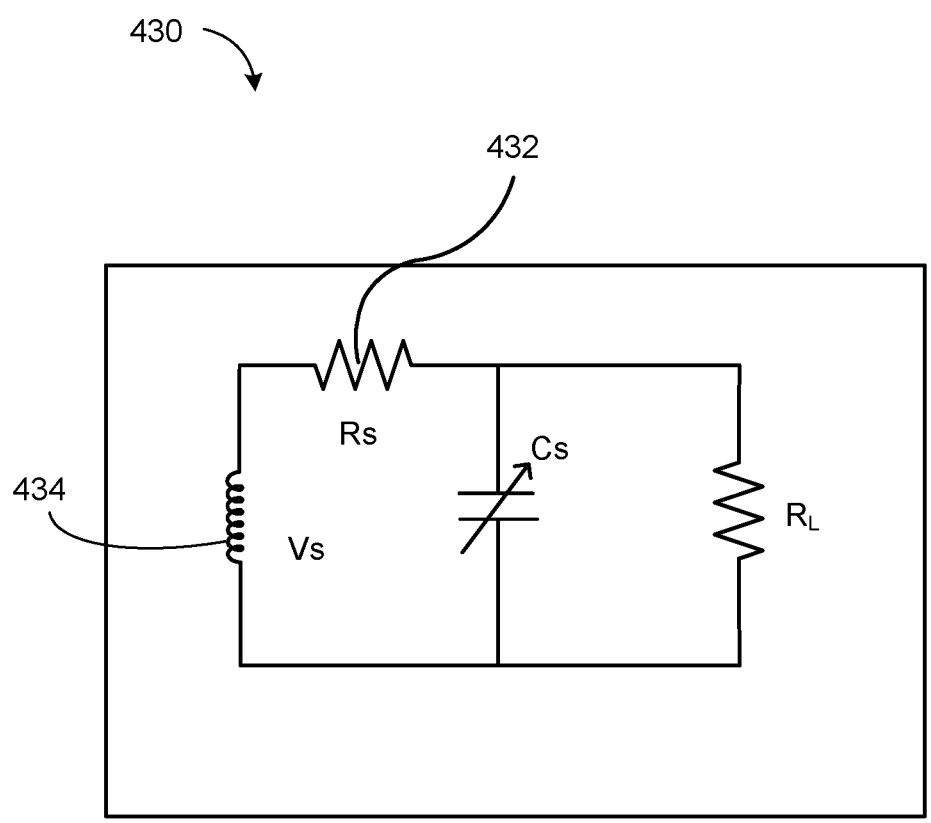
FIG. 5 schematically illustrates a sending unit according to an embodiment.

FIG. 5 is an electrical diagram of a sending unit 430 according to an embodiment. The sending unit 430 may be used in a system or apparatus as described above, such as apparatus 100 or apparatus 200. For example, sending unit 430 may be used in a bodily implant such as bodily implant 310. In the illustrated embodiment, the sending unit 430 includes a pressure sensor 432 (represented as resistor $R_S$) that is configured to detect or sense the fluidic pressure within the inflatable member. In the illustrated embodiment, the sending unit 430 includes a pickup coil 434 (represented as inductor $V_S$). The sending unit 330 does not include a chemical power source, such as battery. In other words, the sending unit 330 is devoid of a battery in which chemical power or energy is converted to electrical power or energy. Accordingly, the sending unit 430 is a passive circuit. The sending unit 430 also includes a load ($R_L$) and a variable capacitor ($C_S$).

Figure 6:
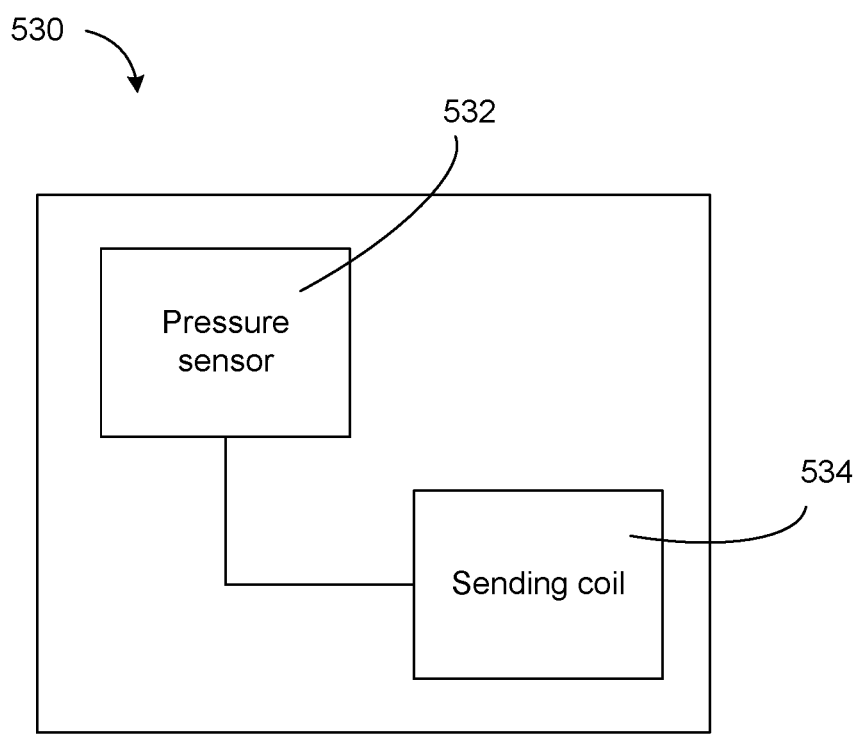
FIG. 6 is a box diagram of a sending unit according to an embodiment.

FIG. 6 is a box diagram of a sending unit 530 according to an embodiment. The sending unit 530 may be used in a system or apparatus as described above, such as apparatus 100 or apparatus 200. For example, sending unit 530 may be used in a bodily implant such as bodily implant 310. In the illustrated embodiment, the sending unit 530 includes a pressure sensor 532 that is configured to detect or sense the fluidic pressure within the inflatable member. In the illustrated embodiment, the sending unit 530 includes a pickup or sending coil 534. The pickup or sending coil 534 is operatively coupled to the pressure sensor 532. In the illustrated embodiment, the sending unit 530 does not include a chemical power source, such as battery. In other words, the sending unit 530 is devoid of a battery in which chemical power or energy is converted to electrical power or energy.

Figure 7:
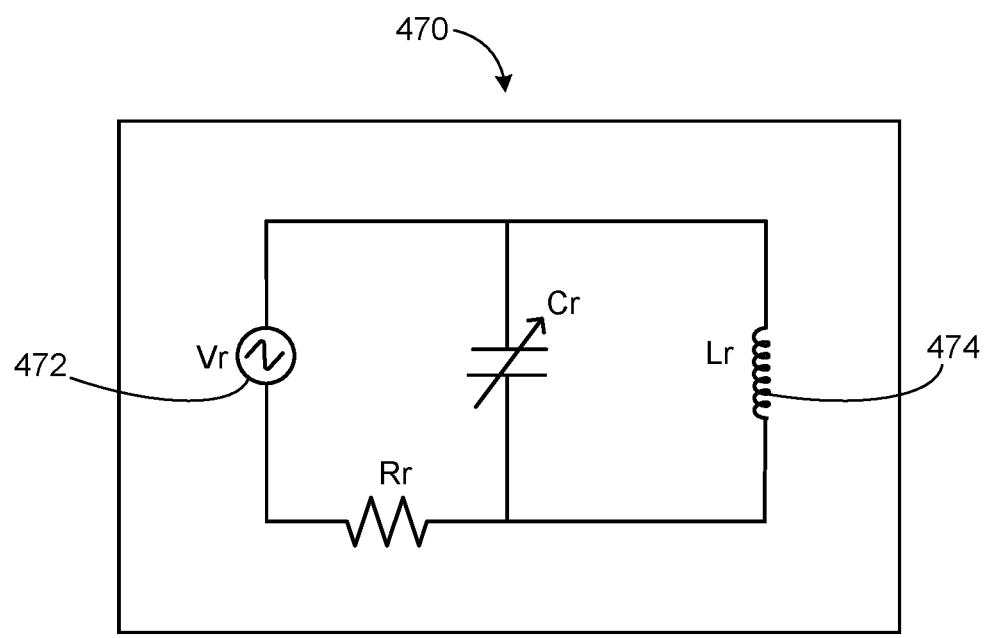
FIG. 7 schematically illustrates a reading unit according to an embodiment.

FIG. 7 is an electrical diagram of a receiving unit 470 according to an embodiment. The receiving unit 470 may be used in a system or apparatus as described above, such as apparatus 100 or apparatus 200. The receiving unit 470 includes a power source 472, such as a battery. In some embodiments, the power source or battery is configured to convert chemical power or energy to electrical power or energy. The receiving unit 470 also includes a pickup coil 474 (represented as inductor Lr). The pickup coil 474 is configured to interact (e.g., inductively interact) with the pickup coil of the sending unit. Specifically, the pickup coil 474 may be tuned to form a circuit with the pickup coil of the sending unit and thereby establish a communication channel or link between the sending unit and the receiving unit 470. The receiving unit 470 also includes a communication mechanism, such as a Bluetooth communication system, that is configured to engage and deliver data to a display device. The receiving unit 470 also includes a resistor (Rr) and a variable capacitor (Cr).

Figure 8:
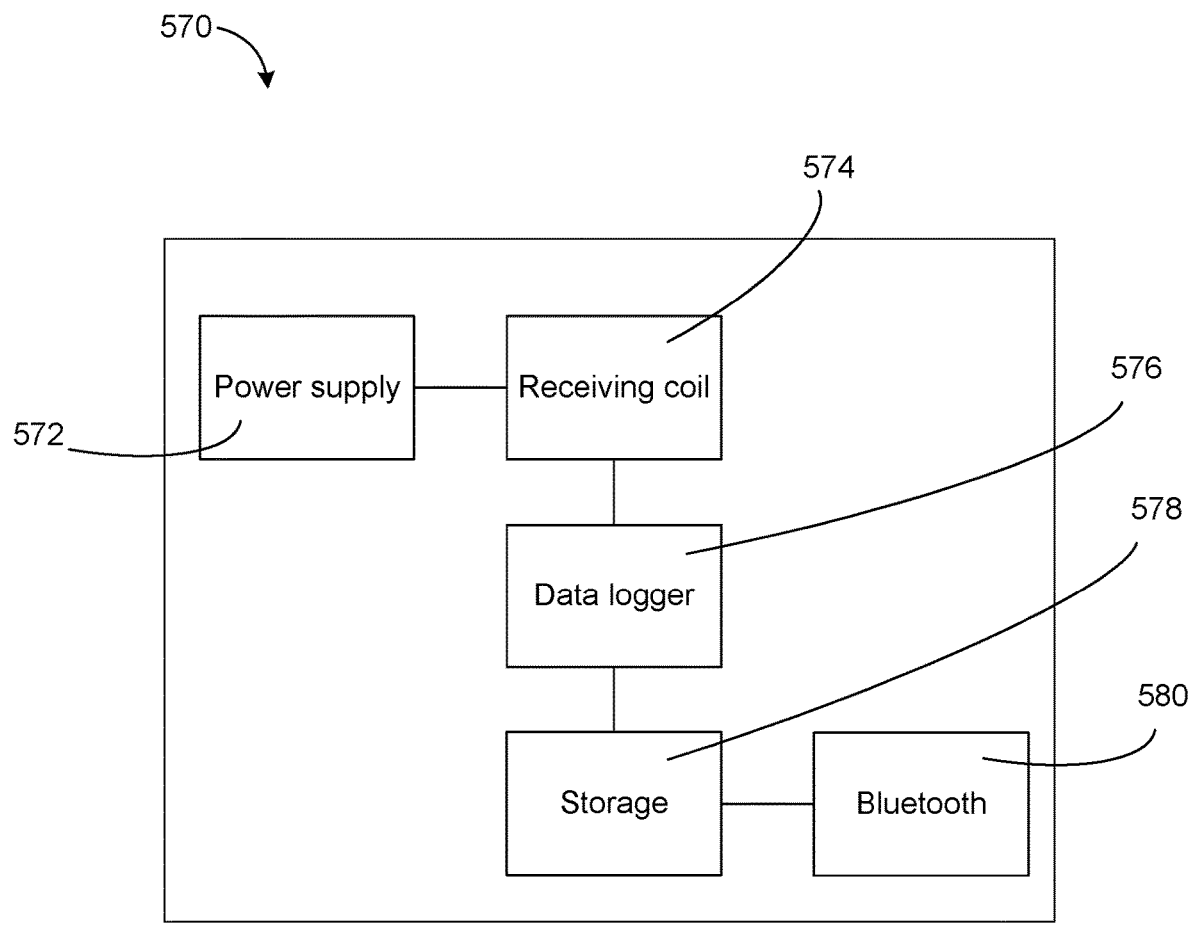
FIG. 8 is a box diagram of a reading unit according to an embodiment.

FIG. 8 is a box diagram a receiving unit 570 according to an embodiment. The receiving unit 570 may be used in a system or apparatus as described above, such as apparatus 100 or apparatus 200. The receiving unit 570 includes a power source or a power supply 572. In some embodiments, the power source or power supply 572 is a battery or other device that is configured to convert chemical power to electrical power. The power source or battery 572 is configured is configured to provide power to the receiving unit 570. The receiving unit 470 also includes a pickup or receiving coil 574. The pickup or receiving coil 574 is configured to interact with the pickup coil of the sending unit. Specifically, the pickup or receiving coil 574 may be tuned to form a circuit with the pickup coil of the sending unit and thereby establish a communication channel or link between the sending unit and the receiving unit 570.

The receiving unit 570 also includes a data logger 576 and a storage device 578. In some embodiments, the data logger 576 is configured to log data or information received from a sending unit. For example, the data logger 576 may be configured to log pressure and time data received from the sending unit. In some embodiments, the storage device is configured to store or record data or information received from the sending unit. The receiving unit 570 also includes a Bluetooth member 580. The Bluetooth member 580 is configured to establish a communication channel or link to communicate with the display device.

FIG. 9 is a flow chart of a method 600 of using a system according to an embodiment of the invention. At 610, a reading unit is connected to a display device. In some embodiments, the reading unit is wirelessly connected to the display device. For example, in some embodiments, the reading unit is connected to the display device via Bluetooth.

At 620, the reading unit is placed in proximity to the sending unit of the bodily implant. In some embodiments, the sending unit is disposed within the body of the patient and the reading unit is disposed outside of the body of the patient.

At 630, the user can then inflate or deflate the inflatable member of the bodily implant. In some embodiments, the system may prompt the user to inflate or deflate the inflatable member of the bodily implant. The pressure can then be observed, monitored, and/or recorded. In some embodiments, the user or physician may create tests or protocols for monitoring the pressure of the inflatable member. In one embodiment, the test or procedure is as follows.

OUTPUT: "IS THE PUMP DEACTIVATED, YES OR NO?
INPUT: "YES"
OUTPUT: "PUMP PRESSURE=0.0 PSI"
OUTPUT: "ACTIVATE THE PUMP"
OUTPUT: "ENTER TOTAL NUMBER OF SQUEEZES"
INPUT: "1"
OUTPUT: "PUMP PRESSURE=1.4 PSI"
OUTPUT: "ACTIVATE THE PUMP"
OUTPUT: "ENTER TOTAL NUMBER OF SQUEEZES"
INPUT: "2"
OUTPUT: "PUMP PRESSURE=3.2 PSI"

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An apparatus, comprising:
a bodily implant configured to be implanted into a body of a patient, the implant including an inflatable member and a sending unit, the sending unit having a sensor configured to sense a pressure of the inflatable member, the bodily implant includes a pump, a reservoir, a first tubular member and a second tubular member, the first tubular member having a first portion and a second portion, the first portion of the first tubular member extending between the pump and the inflatable member, the second portion of the first tubular member being operatively coupled to the sending unit, the second tubular member extending between the pump and the reservoir; and
a reading unit, the reading unit configured to be disposed outside of the body of the patient and configured to operatively communicate with the sending unit.

2. The apparatus of claim 1, wherein the bodily implant includes a pump and a reservoir.

3. The apparatus of claim 1, wherein the bodily implant includes a pump and a reservoir, the pump being configured to pump fluid from the reservoir to the inflatable member.

4. The apparatus of claim 1, wherein the bodily implant includes a pump, a reservoir, a first tubular member extending between the pump and the inflatable member, and a second tubular member extending between the pump and the reservoir.

5. The apparatus of claim 1, wherein the bodily implant includes a pump, the sending unit being operatively coupled between the pump and the inflatable member.

6. The apparatus of claim 1, wherein the bodily implant includes a pump, the sending unit being operatively coupled between and spaced from the pump and the inflatable member.

7. The apparatus of claim 1, wherein the sending unit includes a coil, the reading unit includes a coil and a power source.

8. The apparatus of claim 1, wherein the reading unit is configured to communicate with a display device.

9. The apparatus of claim 1, wherein the reading unit is configured to communicate wirelessly with a display device.

10. The apparatus of claim 1, wherein the inflatable member is configured to form a ring.

11. The apparatus of claim 1, wherein the inflatable member is a cuff.

12. The apparatus of claim 1, wherein the bodily implant is configured to be disposed within a pelvic region of the patient and inflatable member is configured to be disposed adjacent a urethra of the patient.

13. The apparatus of claim 1, wherein the bodily implant is devoid of an electrical power source.

14. A kit, comprising:
a bodily implant configured to be implanted into a body of a patient, the implant including an inflatable member, a pump, and a sending unit, the sending unit having a sensor configured to sense a pressure of the inflatable member, the sending unit being devoid of an electrical power source, the bodily implant includes a tubular member that includes a first portion and a second portion, the first portion of the tubular member is coupled to and extends between the pump and the inflatable member, the second portion is coupled to the sending unit; and
a reading unit, the reading unit configured to be disposed outside of the body of the patient and configured to operatively communicate with the sending unit, the reading unit including a power source.

15. The kit of claim 14, wherein the pump is fluidically coupled to the inflatable member and the sending unit.

16. The kit of claim 14, wherein the reading unit is configured to communicate with a display device.

17. A kit, comprising:
a bodily implant configured to be implanted into a body of a patient, the implant including an inflatable member, a pump, and a sending unit, the sending unit having a sensor configured to sense a pressure of the inflatable member, the sending unit being devoid of an electrical power source, the bodily implant includes a pump and a reservoir, a first tubular member is coupled to and extends between the pump and the reservoir, a second tubular member is coupled to and extends between the inflatable member and a Y connector, a third tubular member is coupled to and extends between the sending unit and the Y connector, and a fourth tubular member is coupled to and extends between the pump and the Y connector; and
a reading unit, the reading unit configured to be disposed outside of the body of the patient and configured to operatively communicate with the sending unit, the reading unit including a power source, the reading unit being configured to wirelessly communicate with a display device.

* * * * *